United States Patent [19]

Gubelmann et al.

[11] Patent Number: 5,352,819

[45] Date of Patent: Oct. 4, 1994

[54] DEHYDROCYANATION OF ALIPHATIC DINITRILES

[75] Inventors: Michel Gubelmann, Paris; Christian Maliverney, Lyons; Helene Pernot, Paris, all of France

[73] Assignee: Rhone-Poulenc Chimie, Courbevoie Cedex, France

[21] Appl. No.: 63,677

[22] Filed: May 20, 1993

[30] Foreign Application Priority Data

May 20, 1992 [FR] France .................. 92 06391

[51] Int. Cl.$^5$ .......................................... C07C 293/30
[52] U.S. Cl. .................................................... 558/381
[58] Field of Search ........................................ 558/381

[56] References Cited

U.S. PATENT DOCUMENTS

| | | | |
|---|---|---|---|
| 2,407,848 | 9/1946 | Ray | 260/464 |
| 3,347,902 | 10/1967 | Grasselli et al. | 260/465.9 |
| 3,507,902 | 4/1970 | Rennkert et al. | 558/381 |
| 3,657,313 | 4/1972 | Gale | 558/381 |
| 3,795,694 | 3/1974 | Onsager | 558/381 X |

FOREIGN PATENT DOCUMENTS

| | | | |
|---|---|---|---|
| 0004208 | 1/1974 | Japan | 558/381 |
| 0028492 | 7/1974 | Japan | 558/381 |

*Primary Examiner*—Joseph Paul Brust
*Attorney, Agent, or Firm*—Burns, Doane, Swecker & Mathis

[57] ABSTRACT

Branched saturated dinitrile byproducts, e.g. 2-methylglutaronitrile, 2-ethylsuccinonitrile and mixtures thereof, are converted into useful ethylenic nitriles by dehydrocyanating same, in vapor phase, in the presence of an at least partially acidified cation exchange substrate, notably a molecular sieve, clay, acid oxide or lamellar phosphate.

20 Claims, No Drawings

DEHYDROCYANATION OF ALIPHATIC DINITRILES

BACKGROUND OF THE INVENTION

1. Field of the Invention

The present invention relates to the dehydrocyanation of aliphatic dinitriles in the vapor phase, and, more especially, to the dehydrocyanation of branched saturated aliphatic dinitriles. Such dinitriles are often byproducts having little value emanating from the production of linear saturated dinitriles. The dehydrocyanation of such compounds produces ethylenic nitriles which are useful starting materials in processes for the synthesis of linear dinitriles.

2. Description of the Prior Art

U.S. Pat. No. 3,795,694 describes the production of 1,4-dicyanobutene and 2-methyleneglutaronitrile by dehydrocyanation, typically in liquid phase, of 1,2,4-tricyanobutane in the presence of a basic catalyst. This '694 patent also describes the conversion of 2-methyleneglutaronitrile into 1,4-dicyanobutene by means of hydrocyanic acid in the presence of a basic catalyst.

Such a process is not applicable to the saturated branched aliphatic dinitriles, which are byproducts produced in significant amounts and which are currently generally destroyed.

SUMMARY OF THE INVENTION

Accordingly, a major object of the present invention is the provision of unique means for converting undesired dinitrile byproducts into commercially valuable ethylenic nitriles.

Briefly, the present invention features process for the dehydrocyanation of branched saturated dinitriles, comprising contacting at least one of said branched saturated dinitriles, in vapor phase, with an at least partially cation exchange substrate.

DETAILED DESCRIPTION OF PREFERRED EMBODIMENTS OF THE INVENTION

More particularly according to the present invention the branched saturated dinitriles which are subjected to dehydrocyanation are advantageously those having the general formula (I):

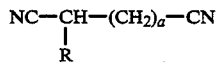  (I)

in which R is a linear or branched alkyl radical having from 1 to 4 carbon atoms, and a is an integer ranging from 1 to 6.

Among the dinitriles of formula (I), prepared are those which are produced in relatively significant amounts in the industrial synthesis of adiponitrile by hydrocyanation of butadiene, and the added value of which presents a serious problem, notably 2-methylglutaronitrile and 2-ethylsuccinonitrile.

Thus, these latter dinitriles are preferably converted in the process of the invention, or mixtures thereof, or industrial mixtures thereof with adiponitrile and/or pentenenitriles.

The temperature at which the process is carried out must be sufficient for the saturated dinitriles to be dehydrocyanated to exist in the vapor state.

Preferably, the reaction temperature ranges from 300° C. to 600° C. and more preferably from 350° C. to 500° C.

In a preferred embodiment of the invention water is introduced simultaneously with the introduction of the saturated dinitrile(s).

The water/branched saturated dinitrile molar ratio advantageously ranges from 0 to 10 and preferably from 0 to 5.

In order to facilitate the introduction of the saturated dinitrile, it is convenient to employ a carrier gas which is inert under the reaction operating conditions.

Nitrogen, either alone or mixed with other inert gases, is typically used.

The catalyst used in the present process is selected from among the partially or completely acidified cation exchangers and, more particularly, from solids having a cation-exchanging capacity of 0.001 to 5 milliequivalents per gram.

The partially or completely acidified cation exchanger substrates characteristically belong to the following families:
(a) the molecular sieves,
(b) the clays,
(c) the pillared clays or bridged clays,
(d) the acid oxides,
(e) the bridged or unbridged lamellar phosphates.

The acidic molecular sieves are more particularly the zeolites of pentasil structure (such as, for example, ZSM-5, ZSM-11, ZSM-22, ZSM-23, ZSM-48, ferrierite and mordenite) and the zeolites of faujasite structure.

The acidic zeolites of pentasil structure are the preferred, especially those of the formula in which the oxide combined with the silica is that of a trivalent metal.

These are more particularly:
(1) the zeolites of ZSM-5 type having the general formula (II), expressed in terms of ratios of oxides:

  (II)

in which M is an element selected from among hydrogen and the mono-, di-, tri- and tetravalent metals, M at least in part being a hydrogen atom, X is a trivalent element selected from among Al, Ga, Fe and B, n is a number ranging from 1 to 4, m is a number equal to or greater than 20, and p is a number ranging from 0 to 40.

(2) the zeolites of ZSM-11 type having the general formula (III), expressed in terms of ratios of oxides:

  (III)

in which M is an element selected from among hydrogen and the mono-, di-, tri- and tetravalent metals, M at least in part being a hydrogen atom, Z is a trivalent element selected from among Al, Ga, Fe and B, n is a number ranging from 1 to 4, m is a number equal to or greater than 20, and x is a number ranging from 6 to 12.

Generally preferred are the zeolites of formula (II) or (III) in which M is selected from among hydrogen, the alkali metals such as, for example, Na, K, Li or Rb, the alkaline earth metals such as, for example, Be, Mg, Ca, Sr or Ba, the rare-earth metals such as, for example, La or Ce, or the transition metals, with the proviso that M at least in part is hydrogen.

In the preferred zeolites of formula (II) or (III), the symbols X and Z represent Al, Ga or B.

Suitable clays are described in FR-A-2,622,575, hereby expressly incorporated by reference.

In the process of the invention, it is preferred to use the smectites such as, for example the montmorillonites, the beidellites, the nontronites, the hectorites, the stevensites and the saponites.

The bridged clays, which are useful catalysts in the subject process, are clays, between the lamellae of which have been introduced bridges or pillars which maintain a basal spacing. The basal spacing is the sum of the thickness of a lamella of the clay and of the interlamellar spacing.

The preparation of these bridged clays is described in FR-A-2,543,446 and in FR-A-2,618,143.

The beidellites will generally be preferred as the starting clay.

The bridging of the clays can be carried out using hydroxides of aluminum, vanadium, molybdenum, zirconium, iron, niobium, tantalum, chromium, lanthanum, cerium, titanium or gallium, or mixed hydroxides of a plurality of these metals.

Preferably, clays are used in the process of the invention, particularly beidellites, which are bridged by means of aluminum hydroxides.

The bridged or unbridged lamellar phosphates which are also useful catalysts in the process of the invention are advantageously phosphates, hydrogenphosphates or sulfophosphonates of zirconium, cerium, thorium, uranium, hafnium, lead, titanium, antimony, germanium or tin, or mixtures of a plurality of these compounds.

The metal sulfophosphonates (or MELS=Molecularly Engineered Layered Structures) are especially those which are described in U.S. Pat. No. 4,235,990.

Among these compounds, particularly advantageous are the zirconium sulfophosphonates described in *Reactive Polymers*, 5, pages 13 to 21 (1987).

The process of the invention is carried out continuously and the flow rate of introduction of the saturated dinitrile into the apparatus is such that it ranges from 0.1 to 10 grams of dinitrile per gram of catalyst per hour (this is the hourly weight productivity of HWP expressed in $h^{-1}$).

The contact time between the saturated dinitrile and the catalyst typically ranges from 0.1 second to 20 seconds.

In order to further illustrate the present invention and the advantages thereof, the following specific examples are given, it being understood that some are intended only as illustrative and in nowise limitative.

EXAMPLES 1 TO 5

Into a quartz tubular reactor having a length of 230 mm and an internal diameter of 15 mm, containing at its lower end a sintered disc and equipped with a casing containing 3 thermocouples, 3 fluid supplies (nitrogen inlet and 2 syringe drivers) and a cylindrical oven, there were successively introduced onto the sintered disc:

(i) quartz grains (having a diameter of 0.8 to 1.2 mm) to a height of 1 to 2 cm;
(ii) the catalyst: 2.31 g (4 cm$^3$) of zeolite of ZSM-5 type (having a cation-exchanging capacity of 0.63 milliequivalent H$^+$/g, a general formula (II) in which M is H and X is Al, a SiO$_2$/Al$_2$O$_3$ molar ratio of 51 and a particle size range of 0.2 to 1.0 mm);
(iii) a second layer of quartz grains to a height of 1 to 2 cm.

The reactants were supplied at a temperature of 450° C.

The inlet flow rates were the following:
(a) nitrogen: 1 liter/hour,
(b) 2-methylglutaronitrile (MGN): 1 gram/hour,
(c) H$_2$O: from 0 to 0.2 gram/hour.

The operating parameters were the following:
(1) hourly weight productivity (HWP): 0.43 h$^{-1}$,
(2) contact times at 450° C.: MGN/N$_2$ 17/83: 4.9 seconds H$_2$O/MGN/N$_2$ 17/14/69: 4.1 seconds The reaction time was on the order of 1 to 2 hours. The products were recovered at the outlet of the apparatus in 3 successive traps (the first cooled to room temperature, the following two by acetone/solid carbon dioxide).

The table below reports the values of the parameters, which varied depending on the tests, and the results obtained.

In this Table, the following conventions were employed:
ct=MGN/catalyst contact time,
DC (%)=degree of conversion of the MGN in %,
RY (%)=DHCN=dehydrocyanation yield in % (sum of pentenenitriles and butenenitriles obtained) with respect to the MGN charged,
RY (%) C=cracking yield in % (sum of the cracking compounds obtained) with respect to the MGN charged,
Sel (%) DHCN=selectivity in % of the dehydrocyanation reaction:

$$\frac{RY(\%)DHCN}{RY(\%)DHCN + RY(\%)C}$$

TABLE

| Examples | Composition of the supply stream (molar %) | | | H$_2$O/MGN Molar ratio | ct (in sec) | DC (%) MGN | RY (%) DHCN | RY (%) C | Sel (%) DHCN |
|---|---|---|---|---|---|---|---|---|---|
| | H$_2$O | MGN | N$_2$ | | | | | | |
| Example 1 | 0 | 17 | 83 | 0 | 4.9 | 28 | 3.5 | 6.4 | 35 |
| Example 2 | 2 | 17 | 81 | 0.12 | 4.8 | 17 | 6.6 | 7.2 | 48 |
| Example 3 | 4 | 17 | 79 | 0.24 | 4.7 | 15 | 7.7 | 5.3 | 59 |
| Example 4 | 12 | 15 | 73 | 0.78 | 4.3 | 15 | 9.1 | 3.8 | 71 |
| Example 5 | 17 | 14 | 69 | 1.2 | 4.1 | 18 | 13.4 | 4 | 77 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the dehydrocyanation of a branched saturated aliphatic dinitrile, comprising contacting at least one such branched saturated aliphatic dinitrile capable of forming an ethylenic mono-nitrile through dehydrocyanation, in the vapor phase, with a catalytically effective amount of an at least partially acidified solid cation exchange substrate capable of effecting dehydrocyanization of said dinitrile and having a cation-exchanging capacity of at least 0.001 milliequivalent per gram, and dehydrocyanating said dinitrile to form an ethylenic mono-nitrile.

2. The process as defined in claim 1, said at least one branched saturated dinitrile having the formula (I):

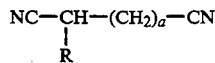

in which R is a linear or branched alkyl radical having from 1 to 4 carbon atoms, and a is an integer ranging from 1 to 6.

3. The process as defined by claim 2, said at least one branched saturated dinitrile of formula (I) comprising 2-methylglutaronitrile, 2-ethylsuccinonitrile, admixture thereof, or admixture thereof with adiponitrile and/or a pentenenitrile.

4. The process as defined by claim 1, carried out at a temperature ranging from 300° C. to 600° C.

5. The process as defined by claim 1, the contacting of said at least one branched saturated dinitrile being carried out in the presence of added water.

6. The process as defined by claim 5, wherein the added water/branched saturated dinitrile molar ratio ranges up to 10.

7. The process as defined by claim 6, wherein the added water/branched saturated dinitrile molar ratio ranges up to 5.

8. The process as defined by claim 1, said at least one branched saturated dinitrile being entrained within an inert carrier gas.

9. The process as defined by claim 1, said at least partially acidified cation exchange substrate comprising solids having a cation-exchanging capacity ranging from 0.001 to 5 milliequivalents per gram.

10. The process as defined by claim 1, said at least partially acidified cation exchange substrate comprising a molecular sieve, a clay, a pillared or bridged clay, an acid oxide, or a bridged or unbridged lamellar phosphate.

11. The process as defined by claim 10, said at least partially acidified cation exchange substrate comprising a zeolite of pentasil or faujasite structure.

12. The process as defined by claim 11, said at least partially acidified cation exchange substrate comprising a zeolite of ZSM-5, ZSM-11, ZSM-22, ZSM-23 or ZSM-48 type, or of ferrierite or mordenite.

13. The process as defined by claim 11, said at least partially acidified cation exchange substrate comprising a zeolite of pentasil structure wherein the silica is combined with an oxide of a trivalent metal.

14. The process as defined by claim 12, said at least partially acidified cation exchange substrate comprising a ZSM-5 zeolite having the formula (II):

$$M_{2/n}O \cdot X_2O_3 \cdot mSiO_2 \cdot pH_2O \qquad (II)$$

in which M is hydrogen or a mono-, di-, tri- or tetravalent metal, with the proviso that M at least in part is hydrogen; X is trivalent Al, Ga, Fe or B; n is a number ranging from 1 to 4; m is a number equal to at least 20; and p is a number ranging from 0 to 40.

15. The process as defined by claim 12, said at least partially acidified cation exchange substrate comprising a ZSM-11 zeolite having the formula (III):

$$M_{2/n}O \cdot Z_2O_3 \cdot mSiO_2 \cdot xH_2O \qquad (III)$$

in which M is hydrogen or a mono-, di-, tri- or tetravalent metal, with the proviso that M at least in part is hydrogen; Z is trivalent Al, Ga, Fe or B; n is a number ranging from 1 to 4; m is a number equal to at least 20; and 4 is a number ranging from 6 to 12.

16. The process as defined by claim 10, said at least partially acidified cation exchange substrate comprising a clay.

17. The process as defined by claim 10, said at least partially acidified cation exchange substrate comprising a bridged clay.

18. The process as defined by claim 10, said at least partially acidified cation exchange substrate comprising an acid oxide.

19. The process as defined by claim 10, said at least partially acidified cation exchange substrate comprising a bridged or unbridged lamellar phosphate.

20. The process as defined by claim 10, said at least partially acidified cation exchange substrate comprising a smectite, beidellite or sulfophosphonate.

* * * * *

UNITED STATES PATENT AND TRADEMARK OFFICE
CERTIFICATE OF CORRECTION

PATENT NO. : 5,362,819

DATED : Nov. 8, 1994

INVENTOR(S) : Douglas S. McBain, Andrew L. Ratermann, I. Glen Hargis, Earl G. Melby and Kevin P. LaJudice It is certified that error appears in the above-indentified patent and that said Letters Patent is hereby corrected as shown below:

Claim 16, column 14 at line 26 insert after the word "block" the following -- are connected by an ester linkage, an amide linkage, a urea linkage, or a urethane linkage, and wherein the Tg of said B block is minus 20°C or less.--

Signed and Sealed this

Twenty-sixth Day of March, 1996

Attest:

BRUCE LEHMAN

Attesting Officer    Commissioner of Patents and Trademarks